United States Patent [19]
Hasslacher et al.

[11] Patent Number: 6,046,042
[45] Date of Patent: Apr. 4, 2000

[54] (S)-HYDROXYNITRILELYASE FROM *HEVEA BRASILIENSIS*

[75] Inventors: Meinhard Hasslacher; Michael Schall; Helmut Schwab; Elfriede Marianne Hayn; Sepp Kohlwein; Herfried Griengl, all of Graz, Austria

[73] Assignee: DSM Chemie Linz GmbH, Linz, Austria

[21] Appl. No.: 08/981,256

[22] PCT Filed: Jul. 10, 1996

[86] PCT No.: PCT/EP96/03010

§ 371 Date: Dec. 22, 1997

§ 102(e) Date: Dec. 22, 1997

[87] PCT Pub. No.: WO97/03204

PCT Pub. Date: Jan. 30, 1997

[30] Foreign Application Priority Data

Jul. 12, 1995 [AT] Austria ..................... 1182/95

[51] Int. Cl.⁷ ............... C12P 13/00; C12N 9/88; C12N 1/20; C07H 21/04

[52] U.S. Cl. .............. 435/128; 435/232; 435/252.3; 435/320.1; 435/280; 435/419; 536/23.2

[58] Field of Search ............... 435/232, 320.1, 435/252.3, 419, 325, 128, 280; 536/23.2

[56] References Cited

U.S. PATENT DOCUMENTS 5,346,816   9/1994   Griengl et al. ............... 435/128

OTHER PUBLICATIONS

Selmar et al. *Physiologia Plantarum*, 75: 97–101, 1989.

*Primary Examiner*—Ponnathapu Achutamurthy
*Assistant Examiner*—Tekchand Saidha
*Attorney, Agent, or Firm*—Wenderoth, Lind & Ponack, L.L.P.

[57] ABSTRACT

A purified (S)-hydroxy-nitrile-lyase is disclosed. Also disclosed is an amino acid sequence for (S)-hydroxy-nitrile-lyase and DNA sequence encoding the same.

12 Claims, No Drawings

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 6 amino acid residues
      (B) TYPE: amino acid
      (C) STRANDEDNESS: single
      (D) TOPOLOGY: linear (xi) SEQUENCE DESCRIPTION: SEQ ID NO:1:

Leu Met Glu Val Phe Pro
1              5

(2) INFORMATION FOR SEQ ID NO:2:

(i) SEQUENCE CHARACTERISTICS:
      (A) LENGTH: 6 amino acid residues
      (B) TYPE: amino acid
      (C) STRANDEDNESS: single
      (D) TOPOLOGY: linear (xi) SEQUENCE DESCRIPTION: SEQ ID NO:2:

Gly Ser Leu Phe Gln Asn
1              5

(2) INFORMATION FOR SEQ ID NO:3:

(i) SEQUENCE CHARACTERISTICS:
    (A) LENGTH: 10 amino acid residues
    (B) TYPE: amino acid
    (C) STRANDEDNESS: single
    (D) TOPOLOGY: linear (xi) SEQUENCE DESCRIPTION: SEQ ID NO:3:

Glu Ile Ala Glu Ile Leu Gln Glu Val Ala
 1               5                   10

(2) INFORMATION FOR SEQ ID NO:4:

(i) SEQUENCE CHARACTERISTICS:
        (A) LENGTH: 1078 base pairs
        (B) TYPE: nucleic acid
        (C) STRANDEDNESS: single
        (D) TOPOLOGY: linear (xi) SEQUENCE DESCRIPTION: SEQ ID NO:4:

```
GAAGAGCACA TATCGATAGT AAAGAGTAAG ATATCATCAG AAAATGGCAT TCGCTCATTT       60
TGTTCTTATT CATACCATAT GCCACGGTGC ATGGATTTGG CACAAGCTCA AACCCCTCCT      120
TGAGGCACTT GGCCACAAGG TTACTGCACT GGACCTTGCA GCAAGCGGCG TTGACCCAAG      180
GCAAATTGAG GAGATTGGCT CATTTGATGA GTATTCTGAA CCCTTGTTGA CGTTCTTGGA      240
GGCACTCCCT CCAGGGGAAA AGGTGATTCT GGTTGGCGAG AGCTGTGGAG GACTCAATAT      300
AGCAATTGCT GCTGATAAAT ACTGTGAAAA GATTGCAGCT GCTGTTTTCC ACAATTCAGT      360
ATTGCCAGAC ACCGAGCACT GCCCATCTTA CGTCGTGGAT AAGCTCATGG AGGTGTTTCC      420
CGACTGGAAA GACACCACGT ATTTTACGTA CACTAAAGAT GGCAAGGAGA TAACTGGATT      480
GAAACTGGGC TTCACGCTTC TGAGGGAAAA TTTATATACC CTTTGCGGTC CTGAGGAATA      540
TGAACTGGCG AAGATGTTGA CAAGGAAGGG ATCATTATTT CAAAATATTT TAGCTAAGCG      600
ACCATTCTTC ACTAAGGAAG GTTACGGATC GATTAAGAAA ATTTATGTGT GGACCGACCA      660
AGACGAAATA TTTTTACCTG AATTTCAACT CTGGCAAATA GAAAACTATA AACCAGACAA      720
GGTTTATAAG GTCGAAGGTG GAGATCATAA ATTGCAGCTT ACAAAGACTA AGGAGATCGC      780
TGAAATTCTC CAAGAGGTGG CTGATACCTA TAATTGACTT CTTTGAGGCT TTTTGTTACT      840
ATTAAGTATG GGAGCAACTA TGAGTTAATA ATCTCACATT TTCAAGTGGG AATTAAGTTG      900
TGCTAAAATA AAGTTGTTTA TTGTGTTGTA ATTTTTTTTT CATTTGAAGT GGGACAGTCT      960
CGCACGCTTT CGAGACTCTT TATTTATATA TATAATGTAA GTGTGTATTT AAGGGAAAGC     1020
TACCCCTATT GTGTAGCTTA TCATGCTTTT CTTTGAATCA AATAAATAAA ACTTATTT      1078
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CCTCCAAGAA CGTCAACAAG                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single (D) TOPOLOGY:  linear (xi) SEQUENCE DESCRIPTION: SEQ ID NO:6:

CATCAAATGA GCCAATCTCC                                              20

(2) INFORMATION FOR SEQ ID NO:7:

(i) SEQUENCE CHARACTERISTICS:
          (A) LENGTH:  20 base pairs
          (B) TYPE:  nucleic acid
          (C) STRANDEDNESS:  single
          (D) TOPOLOGY:  linear (xi) SEQUENCE DESCRIPTION: SEQ ID NO:7:

AATTAACCCT CACTAAAGGG                                              20

(2) INFORMATION FOR SEQ ID NO:8:

(i) SEQUENCE CHARACTERISTICS:
          (A) LENGTH:  33 base pairs
          (B) TYPE:  nucleic acid
          (C) STRANDEDNESS:  single
          (D) TOPOLOGY:  linear (xi) SEQUENCE DESCRIPTION: SEQ ID NO:8:

CCGCTCGAGA AGCTTCAAAG AAGTCAATTA TAG                                33

(2) INFORMATION FOR SEQ ID NO:9:

(i) SEQUENCE CHARACTERISTICS:
          (A) LENGTH:  19 base pairs
          (B) TYPE:  nucleic acid
          (C) STRANDEDNESS:  single
          (D) TOPOLOGY:  linear (xi) SEQUENCE DESCRIPTION: SEQ ID NO:9:

CACGCTTCTG AGGGAAAAT                                               19

(2) INFORMATION FOR SEQ ID NO:10:

(i) SEQUENCE CHARACTERISTICS:
          (A) LENGTH:  26 base pairs
          (B) TYPE:  nucleic acid
          (C) STRANDEDNESS:  single
          (D) TOPOLOGY:  linear (xi) SEQUENCE DESCRIPTION: SEQ ID NO:10:

GGAATTCCAT GGCATTCGCT CATTTT                                       26

(2) INFORMATION FOR SEQ ID NO:11:

(i) SEQUENCE CHARACTERISTICS:
          (A) LENGTH:  20 base pairs
          (B) TYPE:  nucleic acid
          (C) STRANDEDNESS:  single
          (D) TOPOLOGY:  linear (xi) SEQUENCE DESCRIPTION: SEQ ID NO:11:

CCTCCAAGAA CGTCAACAAG                                              20

(2) INFORMATION FOR SEQ ID NO:12:

(i) SEQUENCE CHARACTERISTICS:
          (A) LENGTH:  257 amino acid residues
          (B) TYPE:  amino acid
          (C) STRANDEDNESS:  single
          (D) TOPOLOGY:  linear (xi) SEQUENCE DESCRIPTION: SEQ ID NO:12:

```
Met Ala Phe Ala His Phe Val Leu Ile His Thr Ile Cys His Gly Ala
  1               5                  10                  15

Trp Ile Trp His Lys Leu Lys Pro Leu Leu Glu Ala Leu Gly His Lys
             20                  25                  30

Val Thr Ala Leu Asp Leu Ala Ala Ser Gly Val Asp Pro Arg Gln Ile
         35                  40                  45

Glu Glu Ile Gly Ser Phe Asp Glu Tyr Ser Glu Pro Leu Leu Thr Phe
     50                  55                  60

Leu Glu Ala Leu Pro Pro Gly Glu Lys Val Ile Leu Val Gly Glu Ser
 65                  70                  75                  80

Cys Gly Gly Leu Asn Ile Ala Ile Ala Ala Asp Lys Tyr Cys Glu Lys
                 85                  90                  95

Ile Ala Ala Ala Val Phe His Asn Ser Val Leu Pro Asp Thr Glu His
                100                 105                 110

Cys Pro Ser Tyr Val Val Asp Lys Leu Met Glu Val Phe Pro Asp Trp
            115                 120                 125

Lys Asp Thr Thr Tyr Phe Thr Tyr Thr Lys Asp Gly Lys Glu Ile Thr
        130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
    210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

AGCTTGAATT CGGATCC                                                     17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:14:

AGCTGGATCC GAATTCA                                                     17

(S)-HYDROXYNITRILELYASE FROM *HEVEA BRASILIENSIS*

BACKGROUND OF THE INVENTION

1. Field of the Invention

The carrying out of chemical reactions with the assistance of biological catalysts is becoming increasingly important, especially in those areas of application in which it is possible to exploit the property, which is frequently marked among enzymes, of preferentially converting one of the two enantiomers in reactions with chiral or prochiral components.

One of the enzymes used is the (S)-hydroxy-nitrile-lyase (Hnl) from *Hevea brasiliensis* which catalyzes not only the formation of aromatic but also the formation of aliphatic (S)-cyanohydrins from the corresponding aldehydes or ketones with HCN or HCN donors (EP-A-0 632 130). This is important inasmuch as it is not possible to prepare aliphatic (S)-cyanohydrins with other (S)-hydroxy-nitrile-lyases such as, for example, that from Sorghum bicolor (Tetrahedron Letters, 31: 1249–1252, 1990).

2. Description of the Related Art

The previously known Hnl is prepared from the leaves of *Hevea brasiliensis* by the method of Selmar (Physiologia plantarum 75: 97–101, 1989) and has a molecular weight of 46 kDa (J. E. Poulton in: Cyanide Compounds in Biology [Ciba Foundation Symposium 140], pp 67–91, 1988). However, the enzyme isolated in this way is insufficiently pure for obtaining specific anti-Hnl antibodies or determining amino-acid sequences of the Hnl protein. All attempts to isolate pure HNL [sic] enzyme using other conventional chromatographic purification steps have failed. In all attempts to obtain the enzyme in pure form by ion exchange chromatography with sodium chloride gradient elution, no Hnl activity was detectable in the column eluate. This was successful only after ammonium sulfate was used, in place of the sodium chloride gradient which is otherwise customary, for the elution. The invention accordingly relates to a (S)-hydroxy-nitrile-lyase in purified and isolated form. The Hnl isolated and purified in this way has a molecular weight of 30±1 kDa, a specific activity of 19 IU/mg of protein and comprises the following amino-acid part-sequences:

```
Part-sequence 1: ...-leu-met-glu-val-phe-pro-...              (SEQ ID NO:1)
Part-sequence 2: ...-gly-ser-leu-phe-gln-asn-...              (SEQ ID NO:2)
Part-sequence 3: ...-glu-ile-ala-glu-ile-leu-gln-glu-val-ala [sic](SEQ ID NO:3)
```

This made it possible subsequently, after reverse transcription of mRNA from *Hevea brasiliensis*, to clone a cDNA copy of the hnl gene, which has the following nucleotide sequence, the amino-acid sequence derived therefrom for the Hnl protein being indicated underneath, and the part-sequences determined from the Hnl protein being indicated by underlining.

```
                (-43)G AAG AGC ACA TAT CGA TAG TAA AGA GTA AGA TAT CAT CAG AAA (SEQ ID NO:4)

1/1                                     31/11
ATG GCA TTC GCT CAT TTT GTT CTT ATT CAT ACC ATA TGC CAC GGT GCA TGG ATT TGG CAC
Met ala phe ala his phe val leu ile his thr ile cys his gly ala trp ile trp his (SEQ ID NO:12)

61/21                                   91/31
AAG CTC AAA CCC CTC CTT GAG GCA CTT GGC CAC AAG GTT ACT GCA CTG GAC CTT GCA GCA
lys leu lys pro leu leu glu ala leu gly his lys val thr ala leu asp leu ala ala 121/41                                  151/51
AGC GGC GTT GAC CCA AGG CAA ATT GAG GAG ATT GGC TCA TTT GAT GAG TAT TCT GAA CCC
ser gly val asp pro arg gln ile glu glu ile gly ser phe asp glu tyr ser glu pro 181/61                                  211/71
TTG TTG ACG TTC TTG GAG GCA CTC CCT CCA GGG GGA AAG GTG ATT CTG GTT GGC GAG AGC
leu leu thr phe leu glu ala leu pro pro gly glu lys val ile leu val gly glu ser 241/81                                  271/91
TGT GGA GGA CTC AAT ATA GCA ATT GCT GCT GAT AAA TAC TGT GAA AAG ATT GCA GCT GCT
cys gly gly leu asn ile ala ile ala ala asp lys tyr cys glu lys ile ala ala ala 301/101                                 331/111
GTT TTC CAC AAT TCA GTA TTG CCA GAC ACC GAG CAC TGC CCA TCT TAC GTC GTG GAT AAG
val phe his asn ser val leu pro asp thr glu his cys pro ser tyr val val asp lys 361/121                                 391/131
CTC ATG GAG GTG TTT CCC GAC TGG AAA GAC ACC ACG TAT TTT ACG TAC ACT AAA GAT GGC
leu met glu val phe pro asp trp lys asp thr thr tyr phe thr tyr thr lys asp gly 421/141                                 451/151
AAG GAG ATA ACT GGA TTG AAA CTG GGC TTC ACG CTT CTG AGG GAA AAT TTA TAT ACC CTT
lys glu ile thr gly leu lys leu gly phe thr leu leu arg glu asn leu tyr thr leu
```

```
                                              -continued
481/161                                  511/171
TGC GGT CCT GAG GAA TAT GAA CTG GCG AAG ATG TTG ACA AGG AAG GGA TCA TTA TTT CAA
cys gly pro glu glu tyr glu leu ala lys met leu thr arg lys glu ser leu phe gln 541/181                                  571/191
AAT ATT TTA GCT AAG CGA CCA TTC TTC ACT AAG GAA GGT TAC GGA TCG ATT AAG AAA ATT
asn ile leu ala lys arg pro phe phe thr lys glu gly tyr gly ser ile lys lys ile 601/201                                  631/211
TAT GTG TGG ACC GAC CAA GAC GAA ATA TTT TTA CCT GAA TTT CAA CTC TGG CAA ATA GAA
tyr val trp thr asp gln asp glu ile phe leu pro glu phe gln leu trp gln ile glu 661/221                                  691/231
AAC TAT AAA CCA GAC AAG GTT TAT AAG GTC GAA GGT GGA GAT CAT AAA TTG CAG CTT ACA
asn tyr lys pro asp lys val tyr lys val glu gly gly asp his lys leu gln leu thr 721/241                                  751/251
AAG ACT AAG GAG ATC GCT GAA ATT CTC CAA GAG GTG GCT GAT ACC TAT AAT TGA CTT CTT
lys thr lys glu ile ala glu ile leu gln glu val ala asp thr tyr asn OPA

TGAGGCTTTTTGTTACTATTAAGTATGGGAGCAACTATGAGTTAATAATCTCACATTTTCAAGTGGGAATTAAGTTGTG

CTAAAATAAAGTTGTTTATTGTGTTGTAATTTTTTTTTCATTTGAAGTGGGACAGTCTCGCACGCTTTCGAGACTCTTT

ATTTATATATATAATGTAAGTGTGTATTTAAGGGAAAGCTACCCCTATTGTGTAGCTTATCATGCTTTTCTTTGAATCA

AATAAATAAAACTTATTT
```

The cDNA comprises the complete coding region of the hnl gene with an open reading frame for a polypeptide of 257 amino acids. The molecular weight was calculated to be 29,227 Da from the amino-acid sequence of the coding [sic] protein which was deduced from the DNA sequence determined.

The invention accordingly also relates to a DNA sequence which codes for (S)-hydroxy-nitrile-lyase or is more than 85% identical to this sequence in the region coding for hydroxy-nitrile-lyase. It was obtained by reverse transcription from mRNA. The cDNA is the basis for obtaining enzyme preparations by heterologous expression in various host organisms.

The present invention accordingly also relates to recombinant proteins which can be prepared by heterologous expression of the hnl gene (cDNA) from *Hevea brasiliensis* in suitable microorganisms, preferably in eukaryotic microorganisms.

It has emerged in particular that recombinant Hnl protein which has been prepared by heterologous expression of the *Hevea brasiliensis* hnl gene (cDNA) in eukaryotic microorganisms, such as, for example, in *Saccharomyces cerevisiae* or *Pichia pastoris*, differs distinctly from the natural Hnl protein isolated from the plant *Hevea brasiliensis*. The essential characteristic is that the specific activity of such a recombinant Hnl protein is distinctly higher than the specific activity of the purified natural protein from *Hevea brasiliensis*. The differences are also manifested in the electrophoretic behavior of the proteins. Both on isoelectric focusing and on separation in native polyacrylamide gels, the protein bands of the purified recombinant and natural Hnl proteins are found at different positions. It is assumed that this different behavior is attributable to post-translational modification processes which do not take place identically in the plant and in the microorganisms, and that the higher specific activity of the recombinant Hnl protein is attributable to protein molecules which are modified differently in eukaryotic microorganisms.

EXAMPLE 1

Isolation of pure Hnl protein from *Hevea brasiliensis*

8 g portions of leaves of *Hevea brasiliensis* (stored at −20° C. were homogenized in 80 ml of 20 mM potassium phosphate buffer pH 6.5 with an Omnimixer (10,000 rpm, 1.5 min) while cooling in ice. The resulting extract was kept at 4° C. for 1 hour and then filtered through ladies' nylon stockings to remove the coarse cell constituents. The retentate was washed once again with 20 mM potassium phosphate buffer pH 6.5. Small particles were removed by centrifugation (18,000 rpm, 40 min). The crude protein extract obtained in this way was purified by chromatography in the following sequence:

Ion exchange chromatography

A QAE-Sepharose F.F. column (XK 16, 21 cm, Pharmacia, Uppsala, Sweden) was equilibrated with starting buffer I (10 mM histidine/sulfuric acid pH 6.5, 10% sorbitol). After loading on the sample, the column was washed with at least 50 ml of starting buffer. A linear gradient from 0 to 0.6 M $(NH_4)_2SO_4$ in starting buffer I was used for the elution. Fractions (10 ml) were collected and assayed for Hnl activity, and fractions with Hnl activity were pooled.

Hydrophobic interaction chromatography

A column (XK 26, 11 cm) packed with phenyl-Sepharose low substitution (Pharmacia) was equilibrated with starting buffer H (0.65 M $(NH_4)_2SO_4$ in 0.1 M potassium phosphate buffer pH 6.0). The combined Hnl fractions from the ion exchange chromatography were adjusted to 25% $(NH_4)_2SO_4$ saturation and loaded on. The column was then washed with 200 ml of starting buffer and subsequently eluted with a decreasing linear $(NH_4)_2SO_4$ gradient (in 0.1 M potassium phosphate, pH 6.0). 10 ml fractions were collected and assayed for Hnl activity, and fractions with Hnl activity were pooled.

Exclusion chromatography

A Biogel P150 column (26×34 cm, Biorad, Hercules, Calif.) was equilibrated with 100 mM potassium phosphate buffer pH 6.5. The volume of the enzyme solution was reduced by ultrafiltration (exclusion limit 10,000 Da, Amicon Inc., Beverly, Mass.) before loading on. Elution took place with 100 mM potassium phosphate buffer pH 6.5 at room temperature, collecting fractions (6 ml). The Hnl protein purified in this way now showed only one band at a molecular weight of 30±1 kDa in SDS polyacrylamide gel electrophoresis and had a specific activity of 19 IU/mg.

Assay for Hnl activity

The Hnl enzyme activity was followed via the formation of benzaldehyde from racemic mandelonitrile at 25° C. and pH 5.0. 50 μl of enzyme solution were mixed with 900 μl of 50 mM sodium citrate buffer pH 5.0, and the activity assay was started by adding 100 μl of substrate solution (37.5 mM mandelonitrile in 10 mM sodium citrate buffer pH 3.5, prepared fresh each day). The increase in absorption at 280 nm (measurement with substrate solution without enzyme as reference) was followed for 5 min. 1 IU corresponds to the amount of enzyme which catalyzes the conversion of 1 μmol of benzaldehyde per minute from mandelonitrile under the stated conditions.

EXAMPLE 2
Preparation of an expression cDNA gene bank from *Hevea brasiliensis* mRNA was prepared by standard methods from young leaves from a 10-year old tree of the genus *Hevea brasiliensis* from the botanic garden of the University of Graz (Ausubel et al., Current Protocols in Molecular Biology, Green Publishing Associates and Wiley Interscience, New York, 1990). The cDNA gene bank was prepared using the Zap-cDNA Synthesis Kit and the Gigapack II Gold Packaging Extract (Stratagene Cloning Systems, La Jolla, Calif., U.S.A.) in accordance with the instructions in the documents therefor.

EXAMPLE 3
Isolation of a recombinant plasmid whose expressed protein interacts immunologically with antiserum against *Hevea brasiliensis* hydroxy-nitrile-lyase About 100,000 phages from the cDNA gene bank were investigated in an immune screening by standard methods using a polyclonal anti-Hnl antiserum (rabbits). The specifically bound antibody was visualized using a detection system based on alkaline phosphatase and the chromogenic substrate NBT (nitroblue tetrazolium)/X phosphate(5-bromo-4-chloro-3-indolyl phosphate; 4-toluidine salt) (Boehringer Mannheim Biochemica, Mannheim, FRG). The insert from the phage DNA was transferred from a resulting positive clone in accordance with the protocol "In vivo Excision of pBluescript from Uni-Zap XR" (Stratagene Cloning Systems, La Jolla, Calif., U.S.A.) into the appropriate recombinant plasmid (pHNL-100). The size of the cDNA insert was 1100 bp. pHNL-100 was transformed into *E. coli* SOLR (Stratagene Cloning Systems, La Jolla, Calif., U.S.A.). It was possible by induction with 1 mM IPTG to detect a LacZ-Hnl fusion protein which showed immunoreactivity with the anti-Hnl antiserum and had a molecular weight of about 30–32 kDa, and to detect hydroxy-nitrile-lyase activity of 0.035 IU/mg of protein in the cytosolic protein fractions. All the molecular biological techniques were taken from Ausubel et al. (Current Protocols in Molecular Biology, Greene Publishing Associates and Wiley-Interscience, New York, 1990).

EXAMPLE 4
Sequencing of the cDNA fragment from *Hevea brasiliensis* and cloning of the full-length CDNA using PCR methods The DNA sequencing was carried out by the chain-termination method of Sanger et al. (Sanger et al., PNAS, 74:5463–5467, 1977) using the DyeDeoxy Terminator Cycle Sequencing Kit (Applied Biosystems Inc., Foster City, Calif., U.S.A.) and an automatic DNA Sequencer 373A (Applied Biosystems). It was evident from initial sequence data that the plasmid pHNL-100 contains an incomplete cDNA insert. The missing part in the 5' region was added as described hereinafter: phage DNA was isolated from the *H. brasiliensis* cDNA gene bank and employed as template for a two-stage PCR with two gene-specific primers, i.e primer, and after 1: CCTCCAAGAACGTCAACAAG (SEQ ID NO:5); primer 2: CATCAAATGAGCCAATCTCC (SEQ ID NO:6) and a vector-specific primer T3: AATTAACCCT-CACTAAAGGG (SEQ ID NO: 7). PCR cycle 1: only primer 1 and 40 mg of cDNA gene bank (*H. brasiliensis*) DNA; PCR cycle 2: primer 2 and T3 and ¹⁄₁₀ volume from PCR cycle 1 as DNA template. The DNA resulting from PCR cycle 2 was cut with EcoRI and StyI, and the resulting fragment was cloned into the appropriate region of the plasmid pHNL-100 (cut with EcoRI and StyI). The insert in the resulting construct, which was called pHNL-101, was sequenced completely.

Analysis of the DNA sequence revealed an open reading frame starting with AGT at position 1 and ending with a TGA stop codon at position 772, which codes for a protein of 29,227 Da. The size of this protein correlates with the molecular weight determined for the hydroxy-nitrile-lyase (Hnl) isolated from the leaves of *H. brasiliensis*. The DNA sequence coding for this protein was established as the hnl gene (cDNA) of *H. brasiliensis*.

EXAMPLE 5
Preparation of hydroxy-nitrile-lyase preparations by over-expression of the *H. brasiliensis* hnl gene (cDNA) in *Escherichia coli*

For cloning technique reasons, new restriction cleavage sites were introduced, NcoI in the region of the start codon (position 1) and HindIII after the stop codon (position 783), using standard PCR techniques (replacement of the corresponding regions by the PCR fragments). The template used in both cases was DNA from the plasmid pHNL-101.

3' region: PCR with primer P51-HX (CCGCTCGAGAAGCTTCAAAGAAGTCAATTATAG) (SEQ ID NO:8) and primer P51-3.2 (CACGCTTCTGAGGGAAAAT) (SEQ ID NO:9), cutting of the DNA from the PCR with XhoI and CelII and cloning of the fragment into the plasmid pHNL-101 (cut with XhoI and CelII). The resulting plasmid was called pHNL-102.

5' region: PCR with primer P51-EN (GGAATTCCATGGCATTCGCTCATTTT) (SEQ ID NO: 10) and primer P51-3.1A (CCTCCAAGAACGTCAACAAG) (SEQ ID NO: 11), cutting of the DNA from the PCR with EcoRI and StyI and cloning of the fragment into the plasmid pHNL-102 (cut with EcoRI and StyI). The resulting plasmid was called pHNL-103 and checked by sequencing. The NcoI-HindIII fragment from pHNL-103 was cloned in the last step into the *E. coli* expression vector pSE420 (Invitrogen Corp., San Diego, Calif., U.S.A.). The resulting plasmid pHNL-200 was checked by sequencing and transformed into the *E. coli* strain Top10' (Invitrogen Corp., San Diego, Calif., U.S.A.).

An appropriate transformant was cultured in 100 ml of 2xYT medium (10 g/l NaCl, 10 g/l yeast extract, 16 g/l Bacto tryptone), supplemented with 100 mg/l ampicillin Na salt, in a shaken flask with baffles at 37° C. and 160 rpm to an optical density of $OD_{600}$=0.5. The protein production was induced by adding 1 mM IPTG (isopropyl β-D-thiogalactopyranoside), and the culture was continued after addition of 1% glucose for 3 h under the same conditions. The cells were subsequently harvested by centrifugation and taken up in 4 ml of disruption buffer (50 mM potassium phosphate pH 7.4, 1 mM EDTA [ethylene-diaminetetraacetate], 1 mM PMSF [phenylmethylsulfonyl fluoride], 5% glycerol). Disruption of the cells took place while cooling in ice using an ultrasonic disintegrator (Braun Labsonic 2000) at 45 watts for 3 min. The disruption solution was fractionated into soluble and insoluble constituents by centrifugation at 27,000 g and 4° C. for 15 min in a Sorvall SS-34 rotor and a Sorvall RC-5 centrifuge (DuPont Company, Wilmington, Del., U.S.A.). The soluble fraction contained protein with hydroxy-nitrile-lyase activity (0.15 U/mg of protein). Analysis of the proteins in the soluble and insoluble fractions by SDS polyacrylamide gel electrophoresis and Western blotting revealed that only about 1% of the total heterologous immunoreactive Hnl protein produced was present in the active soluble fraction, while 99% of the immunoreactive Hnl protein was to be found in the insoluble fraction in the form of inactive "inclusion bodies".

Proteins in the insoluble fraction were solubilized by adding 20 ml of denaturation buffer (3.5 M urea, 0.1 M Tris; pH 8.0), and the insoluble constituents were removed by centrifugation (27,000 g and 4° C. for 15 min). The resulting protein solution was dialyzed in several stages, first against the buffer 1 (50 mM potassium phosphate pH 7.4, 1 mM EDTA, 1 M urea) and 5 times against buffer 2 (50 mM potassium phosphate pH 7.4, 1 mM EDTA) at 4° C. The solubilized and renatured protein preparation obtained in this way showed a specific Hnl activity of 0.8 to 1.4 IU/mg of protein.

EXAMPLE 6

Preparation of hydroxy-nitrile-lyase preparations by over-expression of the *H. brasiliensis* hnl gene (cDNA) in *Saccharomyces cerevisiae*

For cloning technical reasons, two new cleavage sites (EcoRI, BamHI) were introduced in the region of the HindIII restriction cleavage site of the plasmid pHNL-103 by ligating the plasmid which had been linearized with HindIII to the adaptor B/E (AGCTTGAATTCGGATCC (SEQ ID NO: 13); AGCTGGATCCGAATTCA) (SEQ ID NO:14). The resulting construct was called pHNL-104 and was checked by sequencing.

The hnl gene (cDNA) was removed as BamHI fragment from the plasmid pHNL-104 and cloned into the yeast expression vector pMA91 (Kingsman et al., Methods in Enzymology, 185:329–341, 1990) which had been linearized with BglII. The resulting plasmid was called pHNL-300 and was checked by sequencing and transformed further into the *S. cerevisiae* laboratory strain W303 D (Hill et al., Yeast, 2:16314 167, 1986). Transformants were cultured on minimal medium without leucine (6.7 g/l yeast nitrogen base w/o amino acids [Difco, U.S.A.], 20 g/l glucose, 20 ml/l amino acid concentrate without leucine [adenine 1.0 g/l, methionine 1.0 g/l, arginine 1.0 g/l, threonine 15.0 g/l, histidine 1.0 g/l, tryptophan 1.0 g/l, uracil 2.0 g/l, lysine 11.5 g/l]). For protein production, the cells were cultured in 100 ml of leucine-free minimal medium in an Erlenmeyer flask with baffles at 30° C. and 150 rpm to an optical density of $OD_{600}$=5.0 and harvested by centrifugation. The cells were suspended in 5 ml of disruption buffer (as in Example 5) and disrupted by the "glass bead method" (Ausubel et al., Current Protocols in Molecular Biology, Greene Publishing Associates and Wiley-Interscience, New York, 1990) in a Merckenschlager (Braun, Melsungen, FRG). A hydroxy-nitrile-lyase activity of 4.62 IU/mg of protein was detectable in the soluble cytosolic fraction. Yeast transformants with the blank plasmid pMA91 served as control, and in this case no cytosolic hydroxy-nitrile-lyase activity was detectable. The aqueous protein preparations prepared in this way were stored at −20° C. Another possibility for long-term storage of the protein preparation comprised freeze-drying of the product after removal of all low molecular weight substances (dialysis at 4° C. against distilled water) or disruption of the yeast cells after suspension in water (Benchtop 3L, VIRTIS Co., Inc., Gardiner, N.Y., U.S.A.). The activity of an enzyme sample resolubilized in disruption buffer (as in Example 5) was in this case almost 100% retained.

Furthermore, it was also easily possible to prepare, starting from the aqueous protein preparations, highly purified recombinant Hnl protein. It was possible in a simple manner, using the same process as described in Example 1, to obtain an enzyme preparation which, on SDS polyacrylamide gel electrophoresis, now shows virtually only one band at 30±1 kDa. Such preparations of recombinant Hnl obtained by overexpression in *S. cerevisiae* showed a specific activity of 22 to 28 IU/mg of protein.

EXAMPLE 7

Preparation of hydroxy-nitrile-lyase preparations by over-expression of the *H. brasiliensis* hnl gene (cDNA) in *Pichia pastoris*

The hnl gene (cDNA) was cloned as EcoRI fragment from the plasmid pHNL-104 into the *P. pastoris* expression vector pHIL-D2 (Invitrogen Corp., San Diego, Calif., U.S.A.) which had been linearized with EcoRI. The construct was called pHNL-400 and was checked by sequencing.

Transformation of the host strain GS115 (His4-), selection of the histidine prototrophs and simultaneously the methanol-utilizing auxotrophs took place in accordance with the documents for the Pichia Expression Kit system (Invitrogen Corp., San Diego, Calif., U.S.A.). From 20 positive transformants it was possible to identify two which produced the hydroxy-nitrile-lyase in high intracellular concentration. The cells were cultured for protein production likewise in accordance with the protocols of the Pichia Expression Kit. The cells which had been harvested by centrifugation were suspended in disruption buffer (as Example 5) to an optical density of $OD_{600}$=50.0 and disrupted by the "glass bead method" (as in Example 6). Hydroxy-nitrile-lyase activity of 16 U/mg of protein was detectable in the soluble cytosolic fraction. The protein preparations prepared in this way could be stored in the same manner as described in Example 6 with negligible losses of activity.

It is possible in a simple manner, by the same process as described in Example 1, to obtain a highly purified enzyme preparation which, on SDS polyacrylamide gel electrophoresis, now showed [sic] virtually only one band at 30±1 kDa. Such preparations of recombinant Hnl obtained by overexpression in *P. pastoris* showed specific activity in the range from 41 to 46 IU/mg of protein.

EXAMPLE 8

Comparison of the recombinant Hnl products

Purified Hnl protein preparations were analyzed by iso-electric focusing with gels 3–9 (Phast System, Pharmacia, Uppsala, Sweden) or by native polyacrylamide gel electrophoresis (7.5% polyacrylamide, tris/glycine buffer pH 8.8). It was found from this that different bands were to be found with different preparations.

On isoelectric focusing, Hnl from *H. brasiliensis* showed one band at an isoelectric point of 4.1. With the recombinant proteins from S. cerevisiae and P. pastoris, two or three bands were found close together, which were located somewhat further towards positions corresponding to basic regions. With recombinant Hnl from P. pastoris, the amount at these shifted positions was found to predominate.

On native polyacrylamide gel electrophoresis, the recombinant proteins from *S. cerevisiae* and *P. pastoris* showed a rather similar behavior. In each case, two bands very close together were identified, flanked by two weak bands identified as specific for Hnl protein by Western blotting (with polyclonal anti-Hnl antiserum). In contrast to this, on analysis of the protein from *H. brasiliensis*, a somewhat diffuse band which had run somewhat further was identifiable.

EXAMPLE 9
Identification of essential amino acids of the hydroxy-nitrile-lyase which are involved in the catalysis Searches in protein data banks (Swissprot, PIR, Genpept) using the search module BLAST (Altschul et al., J. Mol. Biol. 215, 403–410, 1990) and construction of multiple alignments and their statistical analysis using program modules of the GCG software package (Program Manual for the Wisconsin Package, Version 8, September 1994, Genetics Computer Group, 575 Science Drive, Madison, Wis., USA 53711) were performed. The parameters of the GAP Program were as follows: 1) GAP weight: 12, 2) Length weight: 4, 3) Average Match: 2.912, and 4) Average Mismatch: −2.003. These searches and construction of multiple alignments led to the following interpretation. Hydroxy-nitrile-lyase from *Hevea brasiliensis* probably belongs to a large group of structurally related proteins of the α/β hydrolase fold type (Ollis et al., Protein Engineering, Vol. 5, 197–211, 1992). Besides a characteristic tertiary folding, these proteins have a so-called catalytic triad with Asp or Ser or Cys as nucleophilic part of the triad, plus Asp/Glu and His. In order to prove that these amino acids determined from computer predictions are also involved in the catalytic activity of the hydroxy-nitrile-lyase (Glu79, Ser80, Cys81, Aps207 and His235), mutant proteins of the hydroxy-nitrile-lyase were prepared with, in each case, the amino acid alanine at positions 79, 80, 207, 235, and serine at position 81. The mutations were introduced at the level of the plasmid pHNL-104 (see Example 6) using standard PCR methods. For alteration of amino acid positions 79, 80 and 81, in each case a mutant, antisense end primer which also overlaps with the gene-specific restriction cleavage site MunI which is necessary for the subcloning, and a vector-specific polymer (T3), were used (Ausubel et al., Current Protocols in Molecular Biology, Vol. 1 & 2, Greene Publishing Associates and Wiley-Interscience, New York, 1990). A special PCR method was used to alter amino acid positions 207 and 235. This entailed use of a phosphorylated mutant primer in the sense direction, a gene-specific primer which also overlaps with the restriction cleavage site CelII which is necessary for the subcloning, and another vector-specific primer (T7) (Michael S. F., BioTechniques 16, 410–412, 1994). The purification of the PCR products and subcloning took place by standard methods. The resulting mutant hnl gene (cDNA) in the plasmids pHNL-105–pHNL-109 were cloned into the expression plasmid pMA91 (pHNL-302–pHNL-306), and the mutant proteins were produced in Saccharomyces cerevisiae as described in Example 6. The hydroxy-nitrile-lyase activity was determined in the soluble cytosolic fraction, with the result that each of the 5 mutations which had been carried out led to complete inactivation of the enzyme activity. It can be inferred from this that there is involvement of these amino acids in the direct enzymatic catalysis. Global retention of the protein structure in the mutant proteins by comparison with the unmutated protein [lacuna] verified by virtually identical migration behavior in isoelectric focusing or native polyacrylamide gel electrophoresis (Ausubel et al., Current Protocols in Molecular Biology, Vol. 1 & 2, Greene Publishing Associates and Wiley-Interscience, New York, 1990).

We claim:

1. A purified (S)-hydroxy-nitrile-lyase comprising the amino acid sequence as set forth in SEQ ID NO. 12.

2. The purified (S)-hydroxy-nitrile-lyase as claimed in claim 1, encoded by the DNA sequence as set forth in SEQ ID NO. 4.

3. An isolated polypeptide having at least 80% homology with the amino acid sequence set forth in SEQ ID NO. 12 and possessing (S)-hydroxy-nitrile-lyase activity.

4. An isolated DNA having at least 85% identity with the DNA sequence as set forth in SEQ ID NO. 4 and encoding a polypeptide possessing (S)-hydroxy-nitrile-lyase activity.

5. A vector comprising a DNA sequence selected from the group consisting of: (1) a DNA sequence encoding the amino acid sequence as set forth in SEQ ID NO. 12, (2) the DNA sequence as set forth in SEQ ID NO. 4, (3) a DNA sequence having at least 85% identity with the DNA sequence as set forth in SEQ ID NO. 4 and encoding a protein with (S)-hydroxy-nitrile-lyase activity and (4) a DNA sequence encoding a polypeptide having at least 80% homology with the amino acid sequence set forth in SEQ ID NO. 12.

6. A host cell comprising the vector of claim 5.

7. The host cell as claimed in claim 6, wherein the host cell is a microorganism cell.

8. The host cell as claimed in claim 6, wherein the host cell is from *Saccharomyces cerevisiae* or *Pichia pastoris*.

9. A recombinant protein comprising the amino acid sequence as set forth in SEQ ID NO. 12.

10. A recombinant protein, which is obtained by heterologous expression of the vector of claim 5 in a host cell.

11. A method of producing a purified (S)-hydroxy-nitrile-lyase or a protein with (S)-hydroxy-nitrile-lyase activity comprising:

culturing the host cell of claim 6, isolating the expressed (S)-hydroxy-nitrile-lyase or protein with (S)-hydroxy-nitrile-lyase activity from the cells, and purifying the expressed (S)-hydroxy-nitrile-lyase or protein with (S)-hydroxy-nitrile-lyase activity from the cells.

12. A method of producing (S)-cyanohydrins comprising contacting a purified (S)-hydroxy-nitrile-lyase having the amino acid sequence as set forth in SEQ ID No: 12 with corresponding aldehydes or ketones with HCN or an HCN-donor to form (S)-cyanohydrins.

* * * * *